(12) United States Patent
Ratushny et al.

(10) Patent No.: US 9,101,631 B2
(45) Date of Patent: Aug. 11, 2015

(54) COMBINATION THERAPY BASED ON SRC AND AURORA KINASE INHIBITION FOR THE TREATMENT OF CANCER

(75) Inventors: Vladimir Ratushny, Woodbury, NY (US); Erica A. Golemis, Oreland, PA (US); Ilya G. Serebriiskii, Rockledge, PA (US); Louis M. Weiner, Washington, DC (US); Igor Astsaturov, Philadelphia, PA (US); Andrew Godwin, Leawood, KS (US)

(73) Assignees: Georgetown University, Washington, DC (US); Fox Chase Cancer Center, Jenkintown, PA (US)

( * ) Notice: Subject to any disclaimer, the term of this patent is extended or adjusted under 35 U.S.C. 154(b) by 0 days.

(21) Appl. No.: 13/139,441

(22) PCT Filed: Dec. 14, 2009

(86) PCT No.: PCT/US2009/067941
§ 371 (c)(1),
(2), (4) Date: Jul. 8, 2011

(87) PCT Pub. No.: WO2010/068951
PCT Pub. Date: Jun. 17, 2010

(65) Prior Publication Data
US 2011/0281935 A1    Nov. 17, 2011

Related U.S. Application Data

(60) Provisional application No. 61/122,292, filed on Dec. 12, 2008.

(51) Int. Cl.
*A61K 31/506* (2006.01)
*A61K 31/55* (2006.01)
*A61K 31/713* (2006.01)
*A61P 35/00* (2006.01)
*A61K 31/517* (2006.01)
*A61K 31/7048* (2006.01)
*A61K 45/06* (2006.01)

(52) U.S. Cl.
CPC ............ *A61K 31/517* (2013.01); *A61K 31/506* (2013.01); *A61K 31/7048* (2013.01); *A61K 45/06* (2013.01)

(58) Field of Classification Search
CPC ............ A61K 2300/00; A61K 31/506; A61K 31/517; A61K 31/7048; A61K 45/06
USPC .................................. 514/215, 252.19, 44 A
See application file for complete search history.

(56) References Cited

U.S. PATENT DOCUMENTS

2006/0058358 A1    3/2006   Dumas et al.
2008/0194556 A1    8/2008   Foote

OTHER PUBLICATIONS

Kimura et al, New Tyrosine Kinase Inhibitors in the Treatment of Chronic Myeloid Leukemia, Oct. 2006, Current Pharmaceutical Biotechnology, vol. 7, 5: 371-379.*
Neidle's Cancer Drug Design and Discovery (Elsevier/Academic Press, 2008, pp. 427-431.*
Tari et al. (Bioorganic and Medicinal Chemistry Letters, 17, 2007, pp. 688-691).*
Bradeen et al. (Blood, vol. 108, 2006, pp. 2332-2338).*

(Continued)

*Primary Examiner* — Savitha Rao
(74) *Attorney, Agent, or Firm* — Kathleen D. Rigaut; Robert C. Netter, Jr.; Dann, Dorfman, Herrell & Skillman

(57) ABSTRACT

Compositions which act synergistically to inhibit the growth of cancer cells and methods of use thereof are disclosed.

13 Claims, 7 Drawing Sheets

Dasatinib alone - IC50: 0.6uM +/- 0.22

C1368 alone - IC50: no curve fit

(56) References Cited

OTHER PUBLICATIONS

PubChem entry C1368 Sigma. (Jun. 13, 2007) [Retrieved from the Internet Mar. 17, 2010; <http://pubchem.ncbi.nlm.nih.gov/summary/summary.cgi?sid=24724434&version=1>].

Nawrocki et al. Poster Board III-280: 3198 The Aurora Kinase Inhibitor MLN8237 Has Potent Anticancer Activity in CML and Ph+ ALL Models and Significantly Increases the Efficacy of Nilotinib. America Society of Hematology 50th Annual Meeting and Exposition. Dec. 8, 2008; Poster Board III-280.

* cited by examiner

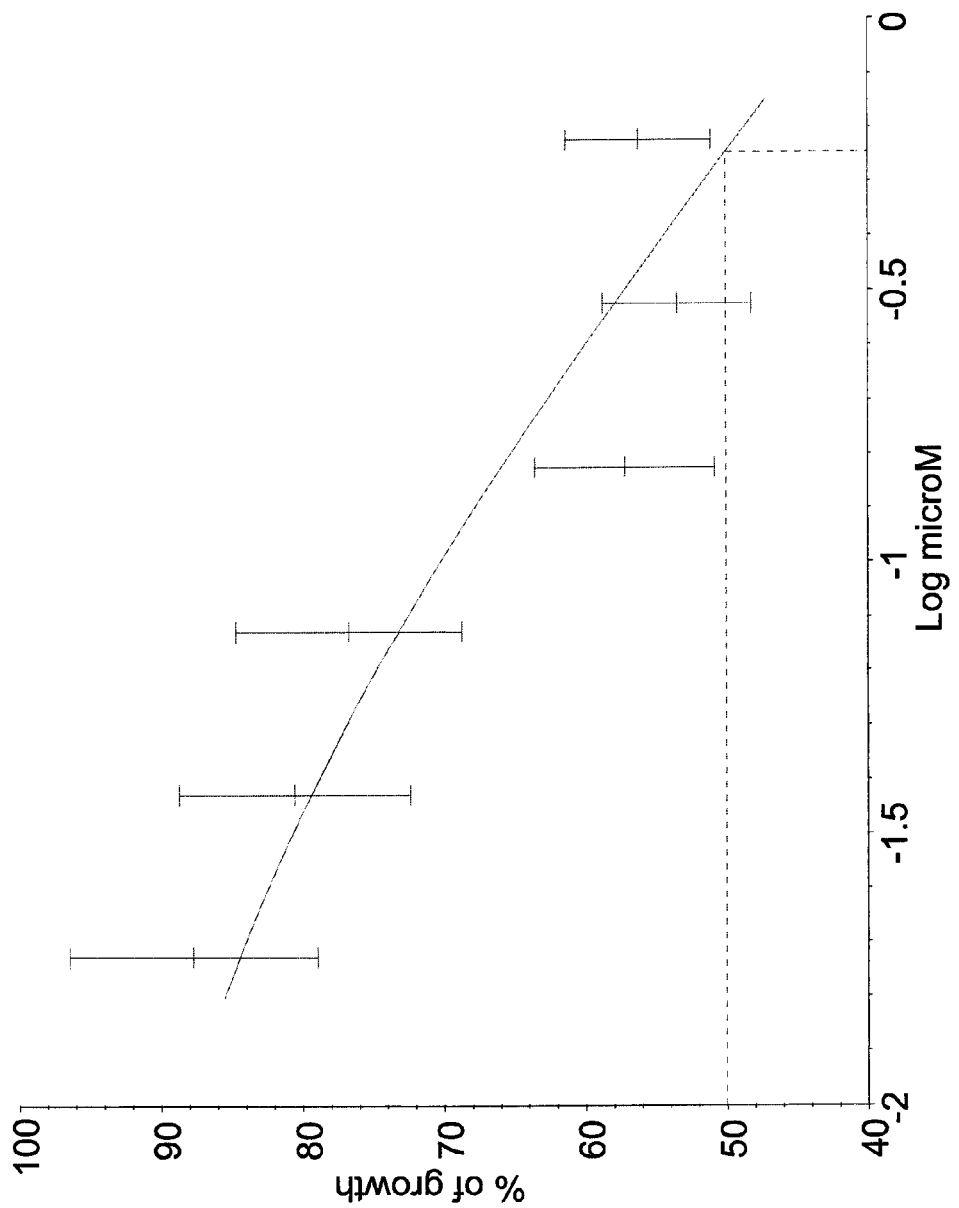

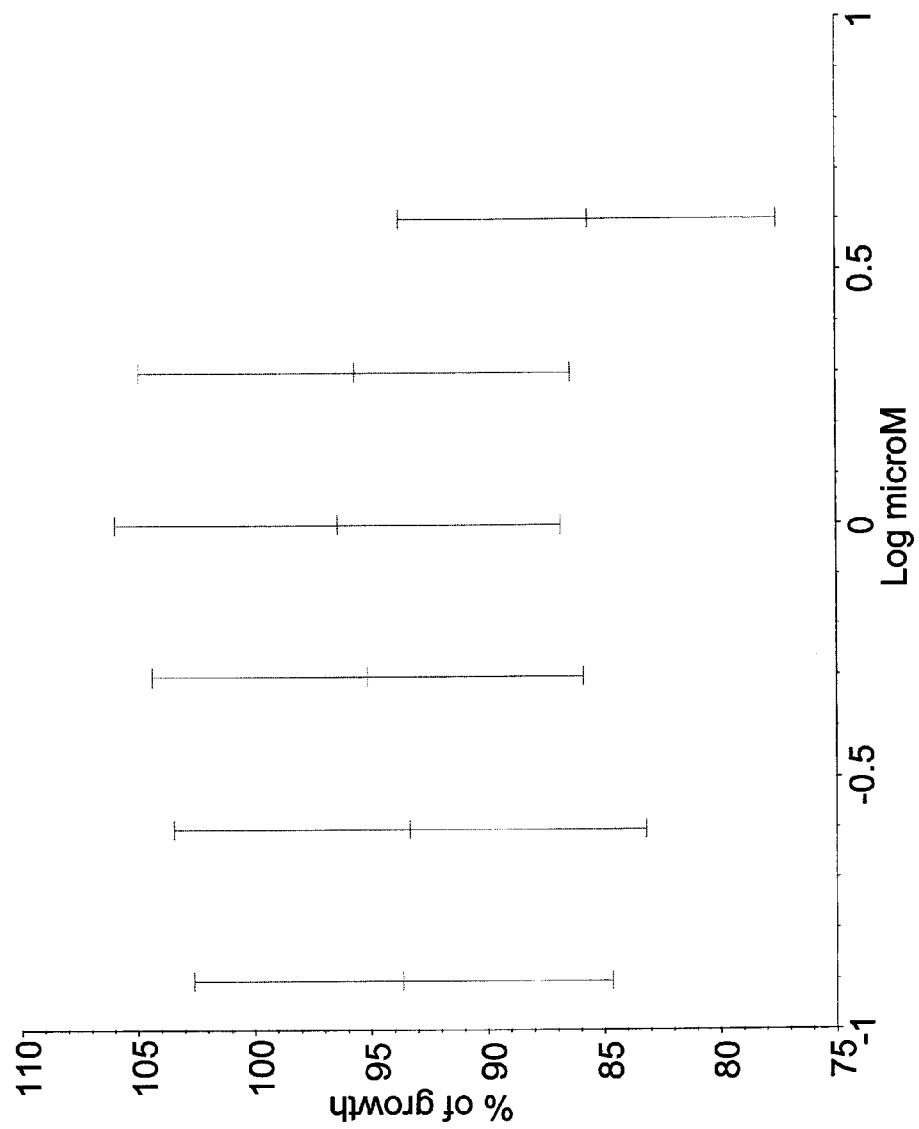

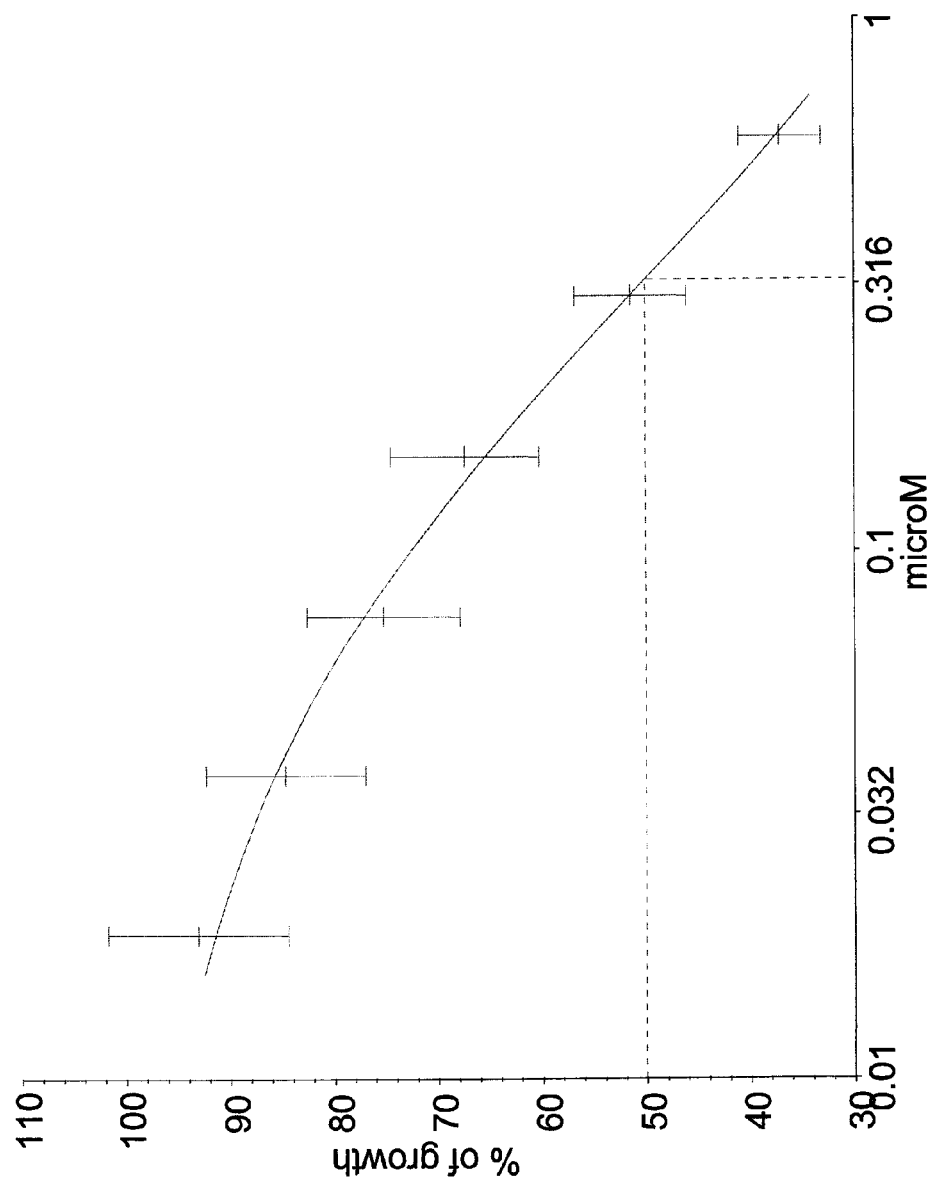

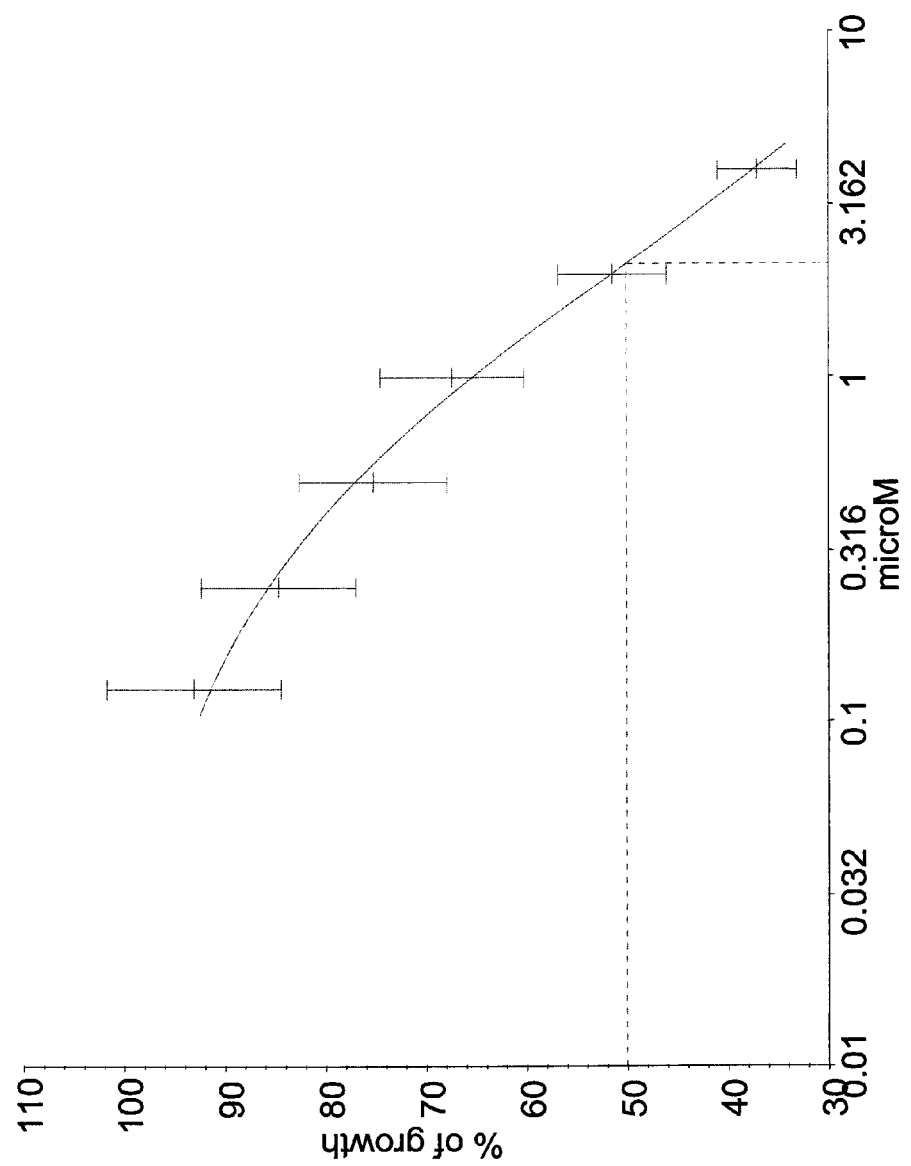

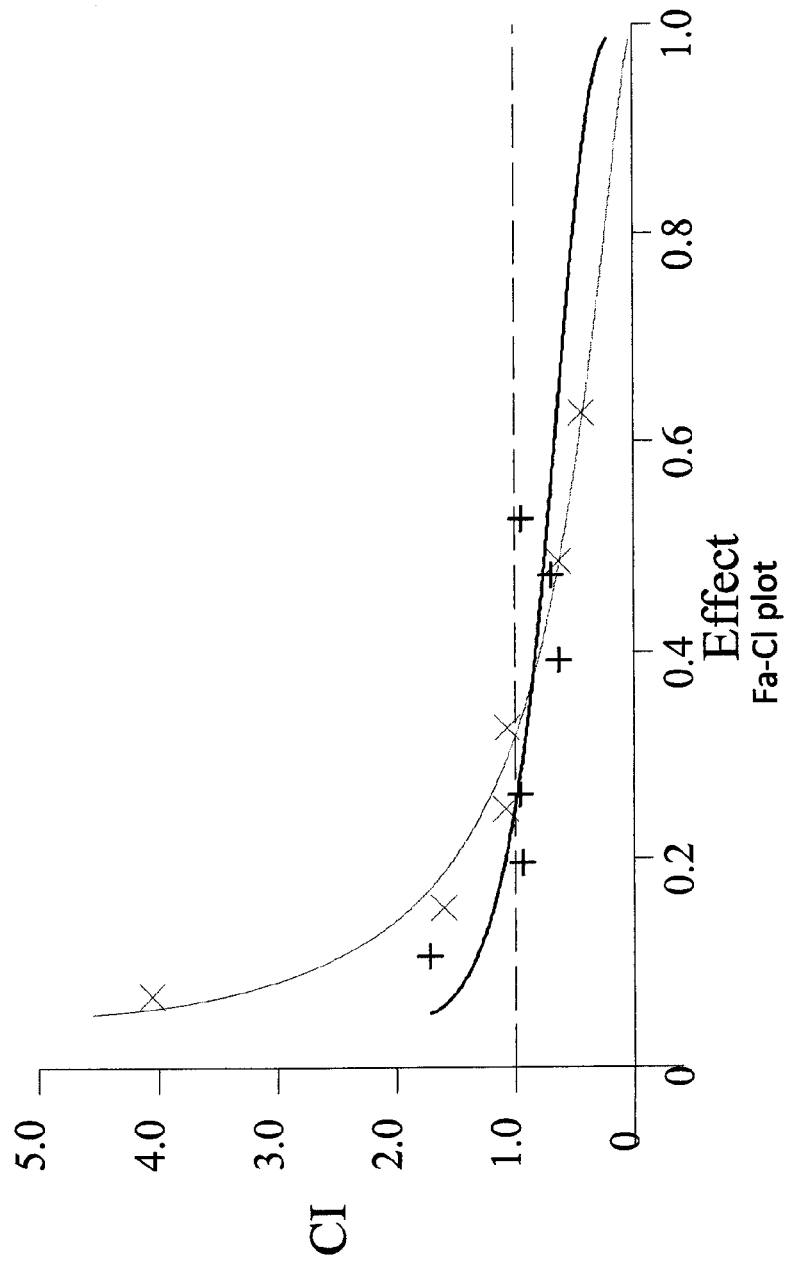

COMBINATION THERAPY BASED ON SRC AND AURORA KINASE INHIBITION FOR THE TREATMENT OF CANCER

This application is a §371 national phase entry of PCT/US2009/067941 filed Dec. 14, 2009, which claims priority to U.S. provisional application 61/122,292 filed Dec. 12, 2008, the entire contents being incorporated herein by reference.

FIELD OF THE INVENTION

The present invention relates to the fields of drug discovery and oncology. More specifically, the invention provides a combination of agents that act synergistically to inhibit the growth of cancer cells and methods of use thereof for the treatment of cancer.

BACKGROUND OF THE INVENTION

Several publications and patent documents are cited throughout the specification in order to describe the state of the art to which this invention pertains. Each of these citations is incorporated herein by reference as though set forth in full.

The National Cancer Institute has estimated that in the United States alone, 1 in 3 people will be struck with cancer during their lifetime. Moreover, approximately 50% to 60% of people contracting cancer will eventually succumb to the disease. The widespread occurrence of this disease underscores the need for improved anticancer regimens for the treatment of malignancy.

In the past several years, Aurora-A kinase (AurA; official name STK6) has attracted increasing attention because it has been found to be overexpressed in a high percentage of tumors arising in breast, colon, ovary, and other tissues and because it has been shown to function as an oncogene when exogenously expressed in various cell line models. AurA overexpression, whether in naturally occurring tumors or following deliberate overexpression, is associated with increased numbers of centrosomes and multipolar spindles, which arise as a consequence of failed cytokinesis. The temporal and spatial localization of overexpressed AurA is not limited to G2 and M phases at the centrosome, but is also detected throughout the cytoplasm in cells in different phases of the cell cycle. Thus, it is not clear at present whether the transforming activity of AurA arises from hyperactivation of normal AurA substrates, or through anomalous targeting by AurA. Unexpectedly, even over-expression of a kinase-inactive form of AurA can induce supernumerary centrosomes (although it cannot transform cells), supporting the idea that the protein has at least two different functions in regulating centrosome numbers: a kinase function, and a scaffolding function for other proteins. Based on these various properties, AurA is now being actively exploited as a target for development of new anti-cancer agents (reviewed in Andrews, P. D. Aurora kinases: shining lights on the therapeutic horizon? Oncogene 2005; 24:5005-15). The AurA-inhibiting compound developed by Nerviano-MS, currently in clinical trials, has been used in the studies described in Soncini, C. et al. (PHA-680632, a novel Aurora kinase inhibitor with potent anti-tumoral activity. Clin Cancer Res 12: 4080-4089, (2006). Sigma also produces a potent Aur-A inhibitor, Cyclopropanecarboxylic acid {3-[4-(3-trifluoromethyl-phenylamino)-pyrimidin-2-ylamino]-phenyl}-amide (hereafter referred to as C1368.)

Despite millions of dollars being spent each year in efforts to identify effective anti-cancer agents and treatment regimens, cancer has yet to be eradicated and effective treatment regimens that are not overly toxic to the patient are still limited in number. It is clear a need exists for improved anti-neoplastic agents and methods of use thereof for the treatment of malignant disease.

SUMMARY OF THE INVENTION

The present invention provides effective therapeutic methods for modulating tumor growth or metastasis wherein a combination of agents is employed. The methods of the present invention provide advantages such as greater overall efficacy, for example, in achieving synergy or avoiding antagonism, and allow, where desired, a reduction in the amount of one or more of the individual agents employed with a concomitant reduction in side effects. Further, where the tumor to be treated is not optimally responsive to a given anticancer agent, use of the present combination therapy methods can nonetheless provide effective treatment.

In particular, the present invention provides a method for modulating tumor growth or metastasis in a patient in need thereof, comprising sequential or simultaneous administration of an aurora kinase A inhibitor (Aur-A inhibitor) and at least one Src kinase inhibitor in amounts effective therefore. Preferred such agents include C1368 from Sigma, PHA680632 from Nerviano and dasatinib from Bristol Myers Squibb described further below. Where simultaneous administration of the Aur-A inhibitor and at least one Src inhibitor is contemplated, the present invention provides pharmaceutical compositions comprising these agents in a subtherapeutic dose for the individual agent, the agents being effective in combination, and providing reduced side effects while maintaining efficacy. Alternatively, each agent can be provided at higher doses for the individual agent, such as those found in the Physician's Desk Reference. Alternatively, where simultaneous or sequential administration of the Aur-A inhibitor and Src inhibitor is contemplated, the present invention further provides a first pharmaceutical composition comprising at least one Aur-A inhibitor and a second pharmaceutical composition comprising at least one Src inhibitor together in a package. Preferably, the Aur-A inhibitor is selected from the group comprising PHA-680632, MLN8237, MK-0457, C1368, ZM 447439, VX-680 and hesparadin and the src inhibitor is dasatinib or other kinase inhibitors with Src selectivity (e.g. AZD0530).

In accordance with the present invention, we have determined that chemical inhibition of Aurora Kinase A with C1368 in HCT116 cells synergizes with src inhibitor dasatinib to effectively inhibit the growth of cancer cells. In vitro, viability-based synergy experiments detected a strong synergy between the two agents with Chou-Talalay derived Coefficient of Interaction (CI) value of <0.5. This effect was not limited to the C1368 as siRNA which down-modulate Aurora kinase expression were also effective in sensitizing ovaran cancer cells to dasatinib mediated src inhibition.

DETAILED DESCRIPTION OF THE INVENTION

Figure 1F:
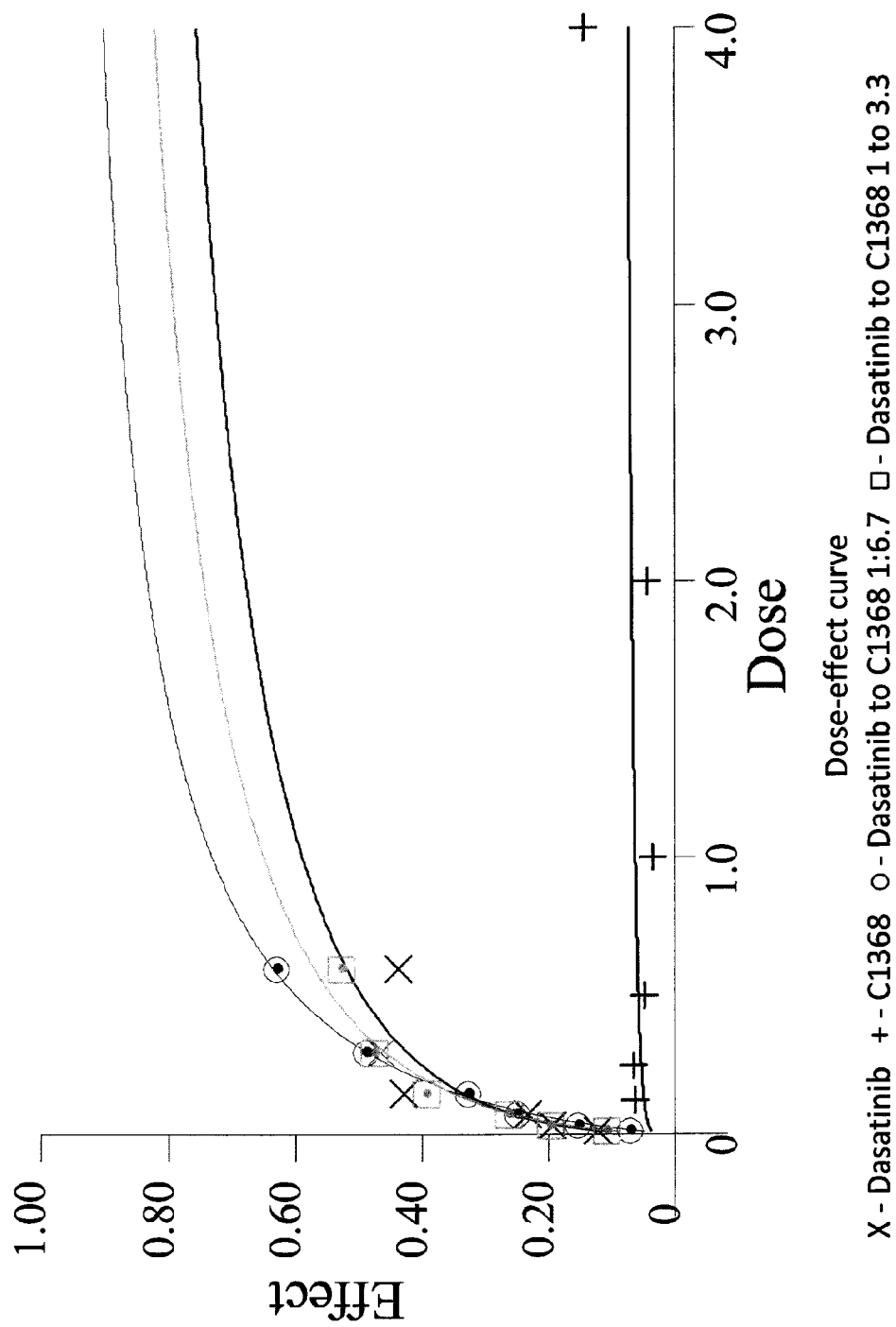
FIG. 1: In vitro synergy assays were performed on HCT116 colorectal cancer cells using dasatinib and C1368 in combination with a ratio of 1:6.7. The $IC_{50}$ value for dasatinib, alone, was determined to be 0.6 (+/−0.22) μM. The $IC_{50}$ value of dasatinib in combination with C1368 was 0.3 μM (+/−0.02). The $IC_{50}$ value for C1368, alone, was undeterminable due to the lack of appreciable cell killing at the concentrations tested. In comparison, the combination of dasatinib: C1368 yielded an $IC_{50}$ values for C1368 at 2.2 (+/−0.10) uM. Using the Chou-Tallalay method, the average Coefficient of Interaction (CI) value for the combinations of the dasatinib: C1368 was 0.35. The CI values indicate that there is strong synergy between C1368 and dasatinib. The Dose-Effect curve shows the stronger effect (increased percentage of HCT116 cell death) at lower doses of drugs when cells are treated with a combination of C1368 and dasatinib than if they are treated with the individual inhibitors. The Fa-CI plot shows that the synergy (lower CI values) between C1368 and dasatinib is most pronounced at doses in which the cell killing (Effect) by the drug combination is greatest.

We have shown that Src inhibitors and Aurora kinase A inhibitors synergistically induce cancer cell death in cell lines derived from multiple human cancer types, including colorectal, and ovarian cancer cells. We treated HCT116 colorectal cancer cells with either Aurora kinase A inhibitor, cyclopropanecarboxylic acid {3-[4-(3-trifluoromethyl phenylamine)-pyrimidin-2-ylamino]-phenyl}-amide (hereafter referred to as C1368, Sigma), or Src inhibitor, dasatinib, or the combination of the two agents. In vitro, viability-based synergy assays detected a strong synergy between the two agents with Chou-Talalay derived Coefficient of Interaction (CI) value of <0.5. We have also shown that siRNA directed to Aurora A or Aurora B or both kinases, sensitizes OVCAR 10 cells to dasatinib.

DEFINITIONS

The phrase "aurora kinase inhibitor" refers to any agent which functions to inhibit or down regulate aurora kinase A and/or aurora kinase B. Such agents include, without limitation, small molecules, chemical compounds and nucleic acid molecules which function to down regulate expression of target genes. Exemplary agents include C1368 from Sigma, MLN8054, PHA-680632 (Nerviano), VX-680, ZM447439, MLN 8237, heparadin, and siRNA which hybridize selectively to aurora kinase encoding mRNA and down regulate expression of the aurora kinase protein product. Exemplary siRNAs that target aurora kinase have the following sequence: Hs_AURKA_1 TCCCAGCGCATTCCTTTG-CAA and Hs_STK6_5 CACCTTCGGCATCCTAATATT.

The phrase "src inhibitor" refers to any agent which is effect to impede or inhibit the function of the src kinase family. Such agents include, without limitation, small molecules, chemical compounds and nucleic acid molecules which function to down regulate expression of target genes and inhibit the function of direct and indirect c-Src substrates, such as the focal adhesion kinase, signal transducer and activator of transcription 3 (STAT3), vascular endothelial growth factor (VEGF), paxillin, Cas, p190RhoGAP, RRas, E-cadherin, c-Jun amino-terminal kinase, NEDD9, and others. Exemplary agents include dasatinib, SU6656, and AZD05530. Src inhibitors are also available from Wyeth and include for example, 4-[(2,4-Dichloro-5-methoxyphenyl) amino]-7-[3-(4-ethyl-1-piperazinyl)propoxy]-6-methoxy-3-quinolinecarbonitrile; 4-[(2,4-Dichloro-5-methoxyphenyl) amino]-6-methoxy-7-[2-(4-methyl-1-piperazinyl)ethoxy]-3-quinolinecarbonitrile; 4-[(2,4-Dichloro-5-methoxyphenyl) amino]-7-[2-(4-ethyl-1-piperazinyl)ethoxy]-6-methoxy-3-quinolinecarbonitrile; 4-[(2,4-Dichloro-5-methoxyphenyl) amino]-6-methoxy-7-[(1-methylpiperidin-4-yl)methoxy]-3-quinolinecarbonitrile; 4-[(2,4-Dichloro-5-methoxyphenyl) amino]-6-methoxy-7-[2-(1-methylpiperidin-4-yl)ethoxy]-3-quinolinecarbonitrile; 4-[(2,4-Dichloro-5-methoxyphenyl) amino]-6-methoxy-7-[3-(1-methylpiperidin-4-yl)propoxy] quinoline-3-carbonitrile; 4-[(2,4-Dichloro-5-methoxyphenyl)amino]-7-[(1-ethylpiperidin-4-yl) methoxy]-6-methoxyquinoline-3-carbonitrile; 4-[(2,4-Dichloro-5-methoxyphenyl)amino]-6-ethoxy-7-[3-(4-methylpiperazin-1-yl)propoxy]quinoline-3-carbonitrile; 4-[(2,4-Dichloro-5-methoxyphenyl)amino]-6-ethoxy-7-[(1-methylpiperidin-4-yl)methoxy]quinoline-3-carbonitrile; 4-[(2,4-Dichloro-5-methoxyphenyl)amino]-6-ethoxy-7-[3-(4-ethylpiperazin-1-yl)propoxy]quinoline-3-carbonitrile; 4-[(2,4-Dichloro-5-methoxyphenyl)amino]-6-ethoxy-7-[3-(1-methylpiperidin-4-yl)propoxy]quinoline-3-carbonitrile; 4-[(2,4-Dichloro-5-methoxyphenyl)amino]-6-ethoxy-7-[2-(4-methyl-1-piperazinyl)ethoxy]quinoline-3-carbonitrile; 4-[(2,4-Dichloro-5-methoxyphenyl)amino]-6-ethoxy-7-[2-(1-methylpiperidin-4-yl)ethoxy]quinoline-3-carbonitrile; or 4-[(2,4-Dichloro-5-methoxyphenyl)amino]-6-methoxy-7-[3-(4-propyl-1-piperazinyl)propoxy]-3-quinolinecarbonitrile; and pharmaceutically acceptable salts thereof.

Suitable compounds possessing inhibitory activity against the Src family of non-receptor tyrosine kinases include the quinazoline derivatives disclosed in International Patent Applications WO 01/94341, WO 02/16352, WO 02/30924, WO 02/30926, WO 02/34744, WO 02/085895, WO 02/092577 (arising from PCT/GB 02/02117), WO 02/092578 (arising from PCT/GB 02/02124) and WO 02/092579 (arising from PCT/GB 02/02128), the quinoline derivatives described in WO 03/008409 (arising from PCT/GB 02/03177), WO 03/047584 and WO 03/048159 and the quinazoline derivatives described in European Patent Applications 02292736.2 (filed 4 Nov. 2002) and 03290900.4 (filed 10 Apr. 2003).

It is disclosed in Journal Medicinal Chemistry, 2001, 44, 822-833 and 3965-3977 that certain 4-anilino-3-cyanoquinoline derivatives are useful for the inhibition of Src-dependent cell proliferation. The 4-anilino-3-cyanoquinoline Src inhibitor known as SKI 606 is described in Cancer Research, 2003, 63, 375.

Other compounds which possess Src kinase inhibitory properties are described in, for example, International Patent Applications WO 96/10028, WO 97/07131, WO 97/08193, WO 97/16452, WO 97/28161, WO 97/32879 and WO 97/49706.

Other compounds which possess Src kinase inhibitory properties are described in, for example, J Bone Mineral Research, 1999, 14 (Suppl. 1), S487, Molecular Cell, 1999, 3, 639-647, Journal Medicinal Chemistry, 1997, 40, 2296-2303, Journal Medicinal Chemistry, 1998, 41, 3276-3292 and Bioorganic & Medicinal Chemistry Letters, 2002, 12, 1361 and 3153.

Particular Src kinase inhibitors include the following:
(i) 4-amino-5-(3-methoxyphenyl)-7-{(4-[2-(2-methoxyethylamino)ethoxy]phenyl)-}-pyrrolo[2,3-d]pyrimidine and 4-amino-5-(3-methoxyphenyl)-7-(4-{(2-[di-(2-methoxyethyl)amino]ethoxy}phenyl)pyrrolo[2,3-d]pyrimidine which are obtainable by methods described in International Patent Application WO 96/10028;

(ii) 4-amino-7-tert-butyl-5-(4-tolyl)pyrazolo[3,4-d]pyrimidine which is also known as PP1 and is described in Molecular Cell, 1999, 3, 639-648;

(iii) 2-(2,6-dichloroanilino)-6,7-dimethyl-1,8-dihydroimidazo[4,5-h]isoquinolin-9-one and 2-(2,6-dichloroanilino)-7-[(E)-3-diethylaminoprop-1-enyl]-6-met-hyl-1,8-dihydroimidazo[4,5-h]isoquinolin-9-one which are obtainable by methods described in Journal Medicinal Chemistry, 2002, 45, 3394;

(iv) 1-[6-(2,6-dichlorophenyl)-2-(4-diethylaminobutyl) pyrido[2,3-d]pyrimidin-7-yl]-3-ethylurea which is obtainable by methods described in Journal Medicinal Chemistry, 1997, 40, 2296-2303 and Journal Medicinal Chemistry, 2001, 44, 1915;

(v) 6-(2,6-dichlorophenyl)-2-[4-(2-diethylaminoethoxy) anilino]-8-methyl-8H-pyrido[2,3-d]pyrimidin-7-one which is also known as PD166285 and is described in J. Pharmacol. Exp. Ther., 1997, 283, 1433-1444;

(vi) the compound known as PD 162531 which is described in Mol. Biol. Cell, 2000, 11, 51-64;

(vii) the compound known as PD166326 which is described in Biochem Pharmacol., 2000, 60, 885-898; and (viii) the compound known as PD173955 which is described in Cancer Research, 1999, 59, 6145-6152.

Other compounds which may possess Src kinase inhibitory properties are described in, for example, International Patent Applications WO 02/079192, WO 03/000188, WO 03/000266, WO 03/000705, WO 02/083668, WO 02/092573, WO 03/004492, WO 00/49018, WO 03/013541, WO 01/00207, WO 01/00213 and WO 01/00214.

Particular Src inhibitors include those provided in International Patent Application WO 01/94341.

Further particular Src inhibitors include the following compounds from International Patent Application WO 02/16352, WO 02/30924, WO 02/30926 and WO 02/34744

Exemplary agents include, without limitation, dasatinib, and AZD0530, and the highly selective, orally available Src/Abl kinase inhibitors cited above. These agents are currently in clinical trials. As used herein, the terms "modulate", "modulating" or "modulation" refer to changing the rate at which a particular process occurs, inhibiting a particular process, reversing a particular process, and/or preventing the initiation of a particular process. Accordingly, if the particular process is tumor growth or metastasis, the term "modulation" includes, without limitation, decreasing the rate at which tumor growth and/or metastasis occurs; inhibiting tumor growth and/or metastasis; reversing tumor growth and/or metastasis (including tumor shrinkage and/or eradication) and/or preventing tumor growth and/or metastasis.

It is to be understood that term "a combination" envisages the simultaneous, sequential or separate administration of the components of the combination. In one aspect of the invention, "a combination" envisages simultaneous administration of the Src inhibitor and an Aurora kinase inhibitor. In a further aspect of the invention, "a combination" envisages sequential administration of those agents. In another aspect of the invention, "a combination" envisages separate administration of those agents. Where the administration of those agents is sequential or separate, the delay in administering the second component should not be such as to lose the benefit of the synergistic effect of the combination therapy. Thus, for the avoidance of doubt, the present invention provides a combination comprising an inhibitor of the Src family of tyrosine kinases, or a pharmaceutically-acceptable salt thereof, and an aurora kinase inhibitor for use simultaneously, sequentially or separately in the synergistic treatment or prophylaxis of cancer.

As used herein, the phrase "effective amount" of a compound or pharmaceutical composition refers to an amount sufficient to modulate tumor growth or metastasis in an animal, especially a human, including without limitation decreasing tumor growth or size or preventing formation of tumor growth in an animal lacking any tumor formation prior to administration, i.e., prophylactic administration.

As used herein, the terms "tumor", "tumor growth" or "tumor tissue" can be used interchangeably, and refer to an abnormal growth of tissue resulting from uncontrolled progressive multiplication of cells and serving no physiological function. A solid tumor can be malignant, e.g. tending to metastasize and being life threatening, or benign. Examples of solid tumors that can be treated or prevented according to a method of the present invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, gastric cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, liver metastases, bile duct carcinoma, choriocarcinoma, seminoma, embryonal carcinoma, thyroid carcinoma such as anaplastic thyroid cancer, Wilms' tumor, cervical cancer, testicular tumor, lung carcinoma such as small cell lung carcinoma and non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Moreover, tumors comprising dysproliferative changes (such as metaplasias and dysplasias) can be treated or prevented with a pharmaceutical composition or method of the present invention in epithelial tissues such as those in the cervix, colon, esophagus, and lung. Thus, the present invention provides for treatment of conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68 to 79). Hyperplasia is a form of controlled cell proliferation involving an increase in cell number in a tissue or organ, without significant alteration in structure or function. For example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. For a review of such disorders, see Fishman et al., 1985, Medicine, 2d Ed., J. B. Lippincott Co., Philadelphia.

Pharmaceutical Compositions

As explained above, the present methods can, for example, be carried out using a single pharmaceutical composition comprising both an Aur-A inhibitor and Src inhibitor (dasatinib) (when administration is to be simultaneous) or using two or more pharmaceutical compositions separately comprising the Aur-A inhibitor and dasatinib (when administration is to be simultaneous or sequential). The phrase "pharmaceutically acceptable" refers to molecular entities and compositions that are physiologically tolerable and preferably do not produce an allergic or similar untoward reaction, such as gastric upset, dizziness and the like, when administered to a human.

Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers, for example to a diluent, adjuvant, excipient, auxiliary agent or vehicle with which an active agent of the present invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

A pharmaceutical composition of the present invention can be administered by any suitable route, for example, by injection, by oral, pulmonary, nasal or other forms of administration. In general, pharmaceutical compositions contemplated to be within the scope of the invention, comprise, inter alia, pharmaceutically acceptable diluents, preservatives, solubilizers, emulsifiers, adjuvants and/or carriers. Such compositions can include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington's Pharmaceutical Sciences, 18th Ed. (1990, Mack Publishing Co., Easton, Pa. 18042) pages 1435-1712 which are herein incorporated by reference. A pharmaceutical composition of the present invention can be prepared, for example, in liquid form, or can be in dried powder, such as lyophilized form. Particular methods of administering such compositions are described infra.

Methods for Modulating Tumor Growth or Metastasis

As explained above, the present invention is directed towards methods for modulating tumor growth and metastasis comprising, the administration of an Aur-A inhibitor such as those listed above and at least one Src inhibitor, preferably dasatinib. The agents of the invention can be administered separately (e.g, formulated and administered separately), or in combination as a pharmaceutical composition of the present invention. Administration can be achieved by any suitable route, such as parenterally, transmucosally, e.g., orally, nasally, or rectally, or transdermally. Preferably, administration is parenteral, e.g., via intravenous injection. Alternative means of administration also include, but are not limited to, intra-arteriole, intramuscular, intradermal, subcutaneous, intraperitoneal, intraventricular, and intracranial administration, or by injection into the tumor(s) being treated or into tissues surrounding the tumor(s).

The Aur-A inhibitor and dasatinib may be employed in any suitable pharmaceutical formulation, as described above, including in a vesicle, such as a liposome [see Langer, Science 249:1527-1533 (1990); Treat et al., in Liposomes in the Therapy of Infectious Disease and Cancer, Lopez-Berestein and Fidler (eds.), Liss: New York, pp. 317-327, see generally, ibid] Preferably, administration of liposomes containing the agents of the invention is parenteral, e.g., via intravenous injection, but also may include, without limitation, intra-arteriole, intramuscular, intradermal, subcutaneous, intraperitoneal, intraventricular, and intracranial administration, or by injection into the tumor(s) being treated or into tissues surrounding the tumor(s).

In yet another embodiment, a pharmaceutical composition of the present invention can be delivered in a controlled release system, such as using an intravenous infusion, an implantable osmotic pump, a transdermal patch, liposomes, or other modes of administration. In a particular embodiment, a pump may be used [see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)]. In another embodiment, polymeric materials can be used [see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. 23:61 (1983); see also Levy et al., Science 228: 190 (1985); During et al., Ann. Neurol. 25:351 (1989); Howard et al., J. Neurosurg. 71:105 (1989)]. In yet another embodiment, a controlled release system can be placed in proximity of the target tissues of the animal, thus requiring only a fraction of the systemic dose [see, e.g., Goodson, in Medical Applications of Controlled Release, supra, vol. 2, pp. 115-138 (1984)]. In particular, a controlled release device can be introduced into an animal in proximity of the site of inappropriate immune activation or a tumor. Other controlled release systems are discussed in the review by Langer [Science 249:1527-1533 (1990)].

The following examples are provided to illustrate certain embodiments of the invention. They are not intended to limit the invention in anyway.

Example I

C1368 (Sigma) is a selective Aurora Kinase inhibitor that has ramifications for cancer therapy because its target, Aurora Kinase A (AurA), plays an important role in mitotic chromosomal segregation and division. Dasatinib (BMS 354-825, Bristol-Myers Squibb) is a small molecule inhibitor of Src kinase. Both over-expression and overactivation of Src have been shown to promote invasion, metastasis in multiple human cancer types. While dasatinib is currently undergoing clinical trials, promising results have been already demonstrated in chronic myeloid leukemias and gastro-intestinal stromal tumors (GIST) patients.

There are no obvious functional connections between the actions of Aurora Kinase inhibitors and Src inhibitors. Our first indication of an interaction between Src and AurA came from experiments designed to test the effects of AurA inhibition on signaling effectors downstream of EGFR. Serum-starved HCT116 cells were stimulated with EGFR ligand, EGF, and cell lysates were immunoblotted with antibody targeting the activating phosphorylation site of Src (serine 418). Even though there was significant constitutive activity of Src at baseline in this Ras-mutated colon cancer cell line, EGF stimulation induced a rapid (5 minutes) and sustained (60 minutes) phosphorylation of Src. Strikingly, cells which were pretreated with an Aur-A inhibitor prior to EGF stimulation exhibited a significant decrease in both basal and EGF-induced phosphorylation of residue serine 418 on Src.

We sought to determine if there was any potential clinical relevance in combining inhibitors of AurA (e.g., C1368) and inhibitors of Src (dasatinib). We performed in vitro synergy assays to test whether C1368 and dasatinib synergize to induce cell death in multiple human cancer cell lines. Individual $IC_{50}$ values for C1368 and dasatinib were obtained in HCT116 cells. Based on their respective $IC_{50}$ values, combination doses of C1368 and dasatinib were determined. Serial dilutions of 1:6.7 and 1:3.3 ratios of dasatinib:C1368 were used in the experiment. The concentrations of dasatinib and C1368 tested ranged from 4 µM to 0.06 µM and 0.6 µM to 0.02 µM, respectively. HCT116 cells were plated at 3000 cells/well concentration into 96 well plates. After allowing 24 hours for cell attachment to occur, cells were treated with serial dilutions of dasatinib, C1368 and 1:6.7 and 1:3.3 combinations of dasatinib and C1368. Cells were incubated for an additional 72 hours and cellular viability measurements were performed using CellTiter Blue assay (Promega). $IC_{50}$ values were calculated using XLFit and CI values were calculated using Calcusyn (Biosoft). See FIG. 1.

The $IC_{50}$ value for dasatinib, alone, was determined to be 0.6 (+/−0.22) µM. The $IC_{50}$ value of dasatinib in combination with C1368 was 0.3 (+/−0.02) and 0.4 (+/−0.05) µM (for 1:6.7 and 1:3.3 combination ratios, respectively). The $IC_{50}$ value for C1368, alone, was undeterminable due to the lack of appreciable cell killing at the concentrations tested. In comparison, 1:6.7 and 1:3.3 combinations of dasatinib:C1368 yielded an $IC_{50}$ values for C1368 at 2.2 (+/−0.10) µM and 1.3 (+/−0.17) µM, respectively. Using the Chou-Tallalay method, the average CI value for the 1:6.7 and 1:3.3 combinations of the dasatinib:C1368 was 0.35 and 0.57, respectively. The CI values indicate that there is strong synergy between C1368 and dasatinib. Results consistent with those described above were observed in DLD1 cells.

Example 2

As mentioned above, a variety of agents have been discovered with effectively inhibit the activity of Aurora A and/or Aurora B kinase. These inhibitors have been assessed for efficacy as anti-cancer agents. As shown in Example 1, we have discovered that combined administration of an aurora kinase inhibitor with a src inhibitor synergistically act to kill cancer c ells. In order to demonstrate that this effect is due to Aurora kinase inhibition and not the particular molecule tested, we also assessed the ability of siRNA which down modulate Aurora kinase expression to sensitize OVCAR10 cells to dasatinib administration.

siRNA transfection was performed in 96-well plates using the reverse transfection protocol. siRNA oligos were diluted with minimal media to yield a final concentration of 5 nM siRNA per well (2.5 nM of each siRNA was used if two siRNA were used in combination). Negative control (siRNA targeting insect luciferase, GL2) and positive controls (cytotoxic siRNA targeting Polo-like kinase 1, PLK1) were included in the plate layout. 0.37 ul of HiPerFect transfection reagent (Qiagen) was used for each well of a 96-well plate. HiPerFect transfection reagent was mixed with siRNA and incubated for 10 minutes at room temperature. OVCAR10 cells were plated on the siRNA/transfection reagent mixture at a cell density of 8000 cells per well in RPMI media with 1% fetal bovine serum. After 24 hour incubation at 37° C., the OVCAR10 cells were either treated with 100 nM dasatinib or vehicle. After an additional 72 hour incubation at 37° C., viability measurements were performed by recording the fluorescence intensity of a metabolite of Alamar blue (Cell-TiterBlue, Promega) using a Perkin Elmer Envision plate reader.

SiRNA sequences:

STK6_5 (Qiagen)   Target Sequences CACCTTCGGCATCCTAATATT

AurB6 (Qiagen)   Target Sequences ACGCGGCACTTCACAATTGAT

GL2 (Thermo)   Sense Sequence CGUACGCGGAAUACUUCGA

PLK1 (Dharmacon)   Sense Sequence CAACCAAAGUCGAAUAUGAUU

TABLE 1

|  | Vehicle | Das 100 nM | Sensitization Ratio |
|---|---|---|---|
| STK6_5 and AurB6 | 0.91 | 0.74 | 0.81 |
| STK6_5 | 0.96 | 0.82 | 0.86 |
| AurB6 | 0.89 | 0.78 | 0.88 |

Figure 2:
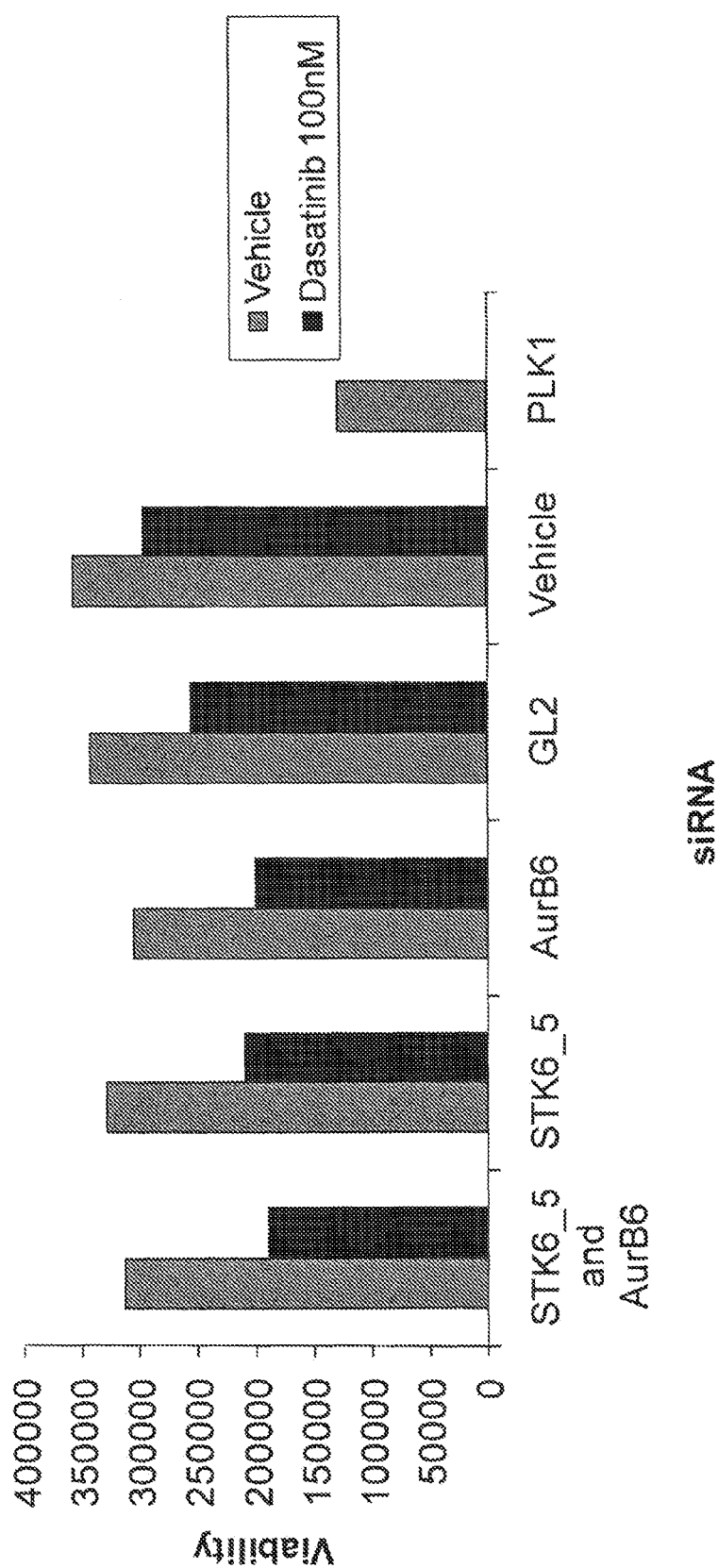
FIG. 2: siRNA targeting Aurora A, Aurora B or a combination of siRNA targeting Aurora-A and B sensitize OVCAR10 cells to dasatinib. OVCAR10 cells were transfected with 5 nM siRNA targeting Aurora A (STK6_5), Aurora B (AurB6), a combination of Aurora A and Aurora B, insect luciferase (GL2, negative control) or Polo-like kinase 1 (PLK1, positive control). Upon 24 hours of incubation at 37° C., the OVCAR10 cells were either treated with 100 nM dasatinib or vehicle and viability measurements were taken after an additional 72 hour incubation at 37° C.

As can be seen in Table 1 and FIG. 2, combined administration of siRNA which inhibit aurora kinase A or B expression with dasatinb effectively sensitized ovarian cancer cells to dasatinb treatment. The greatest decrease in viability was seen in cell treated with either siRNA targeting Aurora A or a combination of Aurora-A and Aurora-B targeted siRNA. Sensitization ratio for each siRNA was determined by dividing the viability dasatinib treated cells normalized to negative control by the viability of vehicle treated cells normalized to negative control. Sensitization ratio=(dasatinib siRNA/dasatinib GL2)/(vehicle siRNA/vehicle GL2). A sensitization ratio of <0.86 was considered as sensitization.

CONCLUSION

The ramifications of our synergistic findings to pharmaceutical firms, and more importantly, to patients are vast. Our synergistic combination can be used to maximize the response rates to two agents which have limited single agent efficacy. The synergistic inhibition of AurA and Src may prove to be useful in multiple cancer types ranging from colorectal cancer, to ovarian, breast, prostate, and head and neck squamous cell carcinoma and chronic myelogenous leukemia.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

What is claimed is:

1. A combination comprising an inhibitor of the Src family of non-receptor tyrosine kinases selected from the group consisting of dasatinib, and AZD0530, or a pharmaceutically-acceptable salt thereof, and an aurora kinase inhibitor selected from the group consisting of C1368, PHA-680632, MLN8237, and Aurora A kinase inhibitory siRNA, or a pharmaceutically acceptable salt thereof for use in the synergistic treatment of colorectal or ovarian cancer.

2. A combination as claimed in claim 1 wherein the Src inhibitor is dasatinib and said Aurora kinase inhibitor is C1368.

3. A combination as claimed in claim 1 wherein the Src inhibitor is dasatinib and said Aurora kinase inhibitor is PHA-680632.

4. A combination as claimed in claim 1 wherein the Src inhibitor is dasatinib and the Aurora kinase inhibitor is MLN8237.

5. A pharmaceutical composition for use in the synergistic treatment or prophylaxis of cancer comprising the combination of claim 1 in a pharmaceutically-acceptable excipient or carrier.

6. A method for the synergistic treatment of colorectal or ovarian cancer in a patient in need of such treatment, comprising the administration of an effective amounts of the combination of claim 1.

7. The method of claim 6, wherein said aurora kinase inhibitor is selected from the group consisting of C1368, PHA-680632, MLN8237, and Aurora A kinase inhibitory siRNA.

8. The method of claim 6, wherein said src inhibitor is selected from the group consisting of dasatinib and AZD0530.

9. The method of claim 6 further comprising administration of an effective amount of at least one anti-cancer agent.

10. The method of claim 6, wherein said agents are administered simultaneously.

11. The method of claim 6, wherein said agents are administered sequentially.

12. The method of claim 6, wherein said patient has colorectal cancer and the Src inhibitor is dasatinib and said Aurora kinase inhibitor is PHA-680632.

13. The method of claim 6, wherein said patient has ovarian cancer and the Src inhibitor is dasatinib and said Aurora kinase inhibitor is PHA-680632.

* * * * *